(12) United States Patent
Yang et al.

(10) Patent No.: US 7,419,690 B2
(45) Date of Patent: Sep. 2, 2008

(54) METHOD FOR ENHANCING PROLIFERATION OF BONE MARROW CELLS OR SPLEEN CELLS WITH AN ETHANOL-INSOLUBLE EXTRACT OF DIOSCOREA

(75) Inventors: Ning-Sun Yang, Taipei (TW); Pei-Fen Su, Keelong (TW); Chin-Jin Li, Taipei (TW); Lie-Fen Shyur, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 11/331,401

(22) Filed: Jan. 12, 2006

(65) Prior Publication Data

US 2006/0105070 A1 May 18, 2006

Related U.S. Application Data

(62) Division of application No. 10/725,823, filed on Dec. 1, 2003, now abandoned.

(51) Int. Cl.
*A61K 36/8945* (2006.01)
*A61K 36/00* (2006.01)

(52) U.S. Cl. ..................... 424/773; 424/725

(58) Field of Classification Search .............. None
See application file for complete search history.

(56) References Cited

FOREIGN PATENT DOCUMENTS

JP 61106516 A * 5/1986

OTHER PUBLICATIONS

Carias, M: Sancocho With Seven Meats; Feb. 17, 2002, URL<http://www.allbaking.net/mf/3/6027> 3 printed pages.*
Pei-Feu et al., Effect of Chinese herbal plant extracts on growth . . . FASEB Journal, (March 7, 2001) vol. 15, No. 4, pp. A673. print., Annual Meeting of Federation of American Societies for Experimental Biologty on Experimental Biology 2001. Orlando, Florida, USA. Mar. 31-Apr. 04, 2001.
Stephens, J. Yams-- Dioscorea spp., University of Flordia IFAS Extension, URL<www.http://edis.ifas.ufl.edu/MV153, pp.1-3.
Michael A. Ang-Lee et al. "Herbal Medicines and Perioperative Care". JAMA 286(2):208-216, Jul. 11, 2001.
Mohsen Araghiniknam et al. "Antioxidant Activity of Dioscorea and Dehydroepiandrosterone (DHEA) in Older Humans". Life Sciences 59(11):147-157, 1996.
Joseph Bolen et al. "Leukocyte Protein Tyrosine Kinases: Potential Targets for Drug Discovery". Annu. Rev. Immunol. 15:371-404, 1997.
Andrea Borchers et al. "Inflammation and Native American medicine: the role of botanicals". Am J Clin Nutr 72:339-347, 2000.
Donald P. Briskin et al. "Medicinal Plants and Phytomedicines. Linking Plant Biochemistry and Physiology to Human Health". Plant Physiology 124:507-514, Oct. 2000.
Xuetao Cao et al. "Augmentation of Hematopoiesis by Fibroblast-Mediated Interleukin-6 Gene Therapy in Mice with Chemotherapy". Journal of Interferon and Cytokine Research 18:227-223, 1998.
Longwen Chen et al. "Oxidative DNA Damage in Prostrate Cancer Patients Consuming Tomato Sauce-Based Entrees as a Whole-Food Intervention". Journal of National Cancer Institute 93(24):1872-1879, Dec. 19, 2001.
N. L. Currier et al. "Deleterious effects of *Echinacea purpurea* and melatonin on myeloid cells in mouse spleen and bone marrrow". Journal of Leukocyte Biology 70:274-276, Aug. 2001.
Jared Gollob et al. "The Functional Synergy Between IL-12 and IL-2 Involves p38 Mitogen-Activated Protein Kinase and Is Associated with the Augmentation of STAT Serine Phosphorylation". The Journal of Immunology 162:4472-4481, 1999.
Larry Karnitz et al. "Interleukin-2 Triggers a Novel Phosphatidylinositol 3-Kinase-Dependent MEK Activation Pathway". Molecular and Cellular Biology 15(6):3049-3057, Jun. 1995.
Jonathan Kelmanson et al. "Zulu medicinal plants with antibacterial activity". Journal of Ethnopharmacology 69:241-146, 2000.
Warren Leonard et al. "JAKS and STATS: Biological Implications". Annu. Rev. Immunol. 16:293-322, 1998.
Manas Majumdar et al. "Isolation, Characterization, and Chondrogenic Potential of Human Bone Marrow-Derived Multipotential Stromal Cells". Journal of Cellular Physiology 185:98-106, 2000.
Sean Morrison et al. "The Long-Term Repopulation Subset of Hematopoietic Stem Cells Is Deterministic and Isolatable by Phenotype". Immunity 1:661-673, Nov. 1994.
Frank Ruschitzka et al. "Acute heart transplant rejection due to Saint John's wort". The Lancet 355:548-549, Feb. 12, 2000.
James Crawley et al. "T Cell Proliferation in Response to Interleukins 2 and 7 Requires p38MAP Kinase Activation". The Journal of Biological Chemistry 272(23):15023-15027, 1997.
Troy Randall et al. "Phenotypic and Functional Changes Induced at the Clonal Level in Hematopoietic Stem Cells After 5-Fluorouracil Treatment". Blood 89(10):3596-3606, 1997.
Gerald Spangrude et al. "Purification and Characterization of Mouse Hematopoietic Stem Cells". Science 241:58-62, Jul. 1, 1988.
David Vistica et al. "Tetrazolium-based Assays for Cellular Viability: A Critical Examination of Selected Parameters Affecting Formazan Production". Cancer Research 51:2515-2520, May 15, 1991.
Yu Wang, MD et al. "Phytochemicals potentiate interleukin-2 generated lymphokine-activated killer cell cytoxicity against murine renal cell carcinoma". Mol. Biother. 4:143-146, Sep. 1992.
Pawel Wlodarski et al. "Role of p53 in Hematopoietic Recovery After Cytotoxic Treatment". Blood 91(8):2998-3006, Apr. 15, 1998.
Z.-Q. Ye et al. "Establishment of an adherent cell feeder layer from human umbilical cord blood for support of long-term hematopoietic progenitor cell growth". Proc. Natl. Acad. Sci. USA 91:12140-12144, Dec. 1994.
Robert Yuan et al. "Traditional Chinese medicine: an approach to scientific proof and clinical validation". Pharmacology & Therapeutics 86:191-198, 2000.

* cited by examiner

*Primary Examiner*—Patricia Leith
(74) *Attorney, Agent, or Firm*—Occhiuti Rohlicek & Tsao LLP

(57) ABSTRACT

A method for enhancing proliferation of bone marrow cells or spleen cells with an alcohol-insoluble extract of a *Dioscorea* plant tuber obtained by stepwise treatment of an aqueous extract of *Dioscorea* plant tuber with aqueous-alcohol solvents.

8 Claims, No Drawings

METHOD FOR ENHANCING PROLIFERATION OF BONE MARROW CELLS OR SPLEEN CELLS WITH AN ETHANOL-INSOLUBLE EXTRACT OF DIOSCOREA

RELATED APPLICATION

This application is a divisional application and claims priority to U.S. application Ser. No. 10/725,823, filed on Dec. 1, 2003 now abandoned, the content of which is incorporated herein in its entirety.

BACKGROUND

The immune system defends the human body against pathogen infection, cellular transformation, and physical/chemical damage. Its impairment, such as decrease in the number of spleen- or bone marrow-derived immune cells, leads to various disorders. The impairment can be caused by aging, disease, and medical treatment (e.g., chemotherapy or immunosuppression). There is a need for drugs that improve the immune system.

SUMMARY

This invention is based, at least in part, on an unexpected discovery that an extract prepared from a tuber of a *Dioscorea* plant enhances the proliferation of bone marrow cells and spleen cells. This extract can be used to improve the immune system.

One aspect of the invention features an extract from a tuber of a *Dioscorea* plant, which is soluble in water and insoluble in an aqueous solution containing 65-90% ethanol, such as 70-80% (e.g., 75%) ethanol, between 0° C. and 25° C. The extract can be prepared from *D. batatas* Decne, *D. alata* L., *D. pseudojaponica*, or *D. alata* L. var. *purpurea* (Roxb.) M. Pouch. In a preferred embodiment, it is prepared from *D. batatas* Decne.

The invention also features a composition containing the just-described extract and a cytokine, e.g., interleukin-2 (IL-2). The composition can be a food product, a food additive, a beverage, a pharmaceutical formulation, or a dietary supplement for improving the immune system.

In another aspect, the invention features a method of enhancing the proliferation of bone marrow or spleen cells. The method includes administering to a subject in need thereof an effective amount of the above-described extract or composition. Examples of the bone marrow cells include colony forming unit-granulocyte macrophage (CFU-GM), colony-forming unit-granulocyte/erythroid/macrophage/megakaryocyte (CFU-GEMM), and burst-forming unit-erythroid (BFU-E) cells. "Administration" refers to intake of the extract or composition in any suitable form (e.g., food product, beverage, and tablet). An "effective amount" refers to an amount of the extract or composition that is sufficient to provide a therapeutic or healthful benefit, i.e., enhancing the proliferation of bone marrow or spleen cells or reducing the probability of relapse after a successful course of treatment.

The details of one or more embodiments of the invention are set forth in the accompanying description below. Other features, objects, and advantages of the invention will be apparent from the description, and from the claims.

DETAILED DESCRIPTION

This invention relates to an extract prepared from *Dioscorea* and its use in enhancing the proliferation of bone marrow cells and spleen cells.

For example, within the scope of this invention is an extract prepared from a tuber of a *Dioscorea* plant. This extract can be prepared according to the procedure descried in the example below. It is soluble in water and insoluble in an aqueous solution containing 65-90% ethanol between 0° C. and 25° C. Many species of the genus *Dioscorea*, such as *D. batatas* Decne, *D. alata*, L., *D. pseudojaponica* can be used. Their cultivation, growth, taxonomy, and agricultural practice are well known in the art. See, e.g., Liu et al. 1995, J. Chinese Med. 6:111-126. The extract can be used alone or in combination with other compound, such as cytokines (e.g., IL-2), to enhance the proliferation of bone marrow cells and spleen cells. Its efficacy can be tested according to the method described in the example below or other methods known in the art. It was unexpected that the extract not only stimulates the proliferation of the cells but also acts synergistically with IL-2 in stimulating the proliferation.

IL-2 is known to induce growth of specific immune cells. Recombinant IL-2 has been used in cancer immunotherapy. However, its use is limited by its high manufacturing cost and severe side effects. There is a need for a safe and inexpensive IL-2 composition. As described in the example below, a *Dioscorea* extract of this invention enhances the cellular activity of IL-2 in a synergistic manner. This synergy allows one to use much less IL-2 than it would require to achieve the same cellular effect. *Dioscorea* has been consumed as food for thousands of years and does not cause undesirable side effects. Further, the *Dioscorea* extract of this invention can be made cost-effectively using the method described herein. Accordingly, a composition containing the extract and IL-2 is expected to be a safer and cheaper alternative to therapies relying on IL-2 only.

Thus, also within the scope of this invention is a composition containing the above-described extract or a cytokine, e.g., IL-2, as an active ingredient. Additional ingredients that can be contained in the composition include other herbal extracts, vitamins, amino acids, metal salts, metal chelates, coloring agents, flavor enhancers, preservatives, and the like.

An extract or composition of this invention can be added directly to foods so that an effective amount of the extract is ingested during normal meals. Any methods known to those skilled in the art can be used to add to or incorporate the compositions of this invention into natural or processed foods, provided that the extract remain effective. For example, the composition of the invention can be made and stored at a temperature from about 0° C. to 4° C. "Food" broadly refers to any kind of material, liquid or solid, that is used for nourishing an animal, and for sustaining normal or accelerated growth of an animal including humans. Many types of food products or beverages, such as, but not limited to, fruit juice, herbal extracts, tea-based beverages, dairy products, soy bean product (e.g., tofu), and rice products, can be used to form compositions containing the extract of the invention.

A composition of this invention can be a pharmaceutical composition that contains a pharmaceutically acceptable carrier, such as a solvent, a dispersion medium, a coating, an antibacterial and antifungal agent, and an isotonic and absorption delaying agent. The composition can additionally include binding agents (e.g., pregelatinized maize starch, polyvinylpyrrolidone, or hydroxypropyl methylcellulose); binders or fillers (e.g., lactose, pentosan, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets or capsules can be coated by methods well known in the art.

An above-described composition can be formulated to be compatible with its intended route of administration, e.g., oral administration. Such a composition can be formulated as discrete units such as capsules, cachets, or tablets, each containing a predetermined amount of the extract, as a powder or granules or as a solution or a suspension in an aqueous liquid, a non-aqueous liquid, an oil-in-water emulsion, or a water-in-oil liquid emulsion. In general, the compositions are prepared by uniformly and intimately admixing the extract with liquid carriers or finely divided solid carriers or both, and then, if necessary, shaping the product into the desired presentation. Liquid preparations for oral administration can take the form of, for example, solutions, syrups, or suspensions; or they can be presented as a dry product for constitution with water or other suitable vehicle before use. For instance, the extract described above can be directly packed into vacuum-sealed bottles for use as liquid compositions. The temperature of the liquid used to reconstitute the dried product should be less than 65° C. The liquid preparations can also be prepared by conventional means with additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates, or sorbic acid). Alternatively, as described below, the preparations can be made to resemble foods, containing buffer salts, flavoring, coloring and sweetening agents as appropriate.

The above-described extract or composition can be used as a medicament for treatment of immune system impairment. It also can be used as a dietary supplement, health food, or health drink for prevention of immune system impairment. Subjects to be treated can be identified as having, or being at risk for acquiring, a condition characterized by immune system impairment, e.g., low level of spleen- or bone marrow-derived cells.

For example, patients undergoing chemotherapies or immune-suppressing therapies have low level of immune cells and often suffer from disorders associated with immune system impairment. To restore the immune cell level after the therapies, the patients can be treated with the extract or composition of this invention. In an ex vivo approach, the composition is administered to tissues (e.g., blood and bone marrow) or cells (e.g., tumor infiltrating lymphocytes or lymphokine-activated killer cells) obtained from a subject. The tissues or cells are then introduced back into the subject. In an in vivo approach, a composition of the invention is administered orally or by intravenous infusion, or injected or implanted subcutaneously, intramuscularly, intrathecally, intraperitoneally, intrarectally, intravaginally, intranasally, intragastrically, intratracheally, or intrapulmonarily. This treatment can be performed alone or in conjunction with other drugs or therapy. The term "treating" is defined as administration of a composition to a subject with the purpose to cure, alleviate, relieve, remedy, prevent, or ameliorate a disorder, the symptom of immune system impairment, the disease state secondary to the disorder, or the predisposition toward the disorder.

The efficacy of an extract or composition of this invention can be evaluated for its ability to enhance the proliferation of bone marrow cells and spleens cells in the manner described in the example below. Based on the results, an appropriate dosage range and administration route can be determined.

To determine optimal administration doses and routes, animal studies or clinical trials can also be conducted. The dosage required depends on the choice of the route of administration; the nature of the formulation; the nature of the subject's illness; the subject's size, weight, surface area, age, and sex; other drugs being administered; and the judgment of the attending physician. It can be adjusted by one skilled in the art, e.g., a nutritionist, dietician, or treating physician, in conjunction with the subject's response. Suitable dosages are in the range of 0.01-100.0 mg/kg. Wide variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Preparation of *Dioscorea* Extracts

Three species of the genus *Dioscorea* (*D. batatas* Decne, *D. alata*, L. and *D. pseudojaponica*) and one cultivar of *D. alata* (*D. alata* L. var. *purpurea* (Roxb.) M. Pouch.) were used to prepare extracts. The authenticity of all *Dioscorea* plant materials was validated by Dr. Sin-Yie Liu at Taiwan Agricultural Research Institute.

Tubers of *Dioscorea spp.* were peeled, sliced (2-4 mm), frozen at −80° C., lyophilized, and stored in a desiccator at room temperature until use. The tuber slices were ground to powder. Ten grams of the powder was mixed with 100 ml milli Q water, stirred for 1 hour (h) at room temperature, and centrifuged at 24,000×g at 4° C. for 20 min. The resultant supernatant was filtered through glass wool. The pellet was resuspended in 100 ml water, stirred, centrifuged, and re-extracted in the manner described above. The supernatants from the two extractions were pooled to generate a crude extract (CE) fraction. The CE fraction was further extracted stepwise with 50%, 75%, and 87.5% (V/V) ethanol. The ethanol-insoluble fractions were collected by centrifugation at 24,000×g at 4° C. for 20 min. The pellets were lyophilized and dissolved in sterilized water at a concentration of 10 mg/ml. These fractions were designated as DsCE-I, -II, and -III, respectively. The yields of CE, DsCE-I, -II, and -III were 16.64%, 4.34%, 2.24%, and 1.82% of the dry weight of the starting material.

DsCE-II Stimulated Growth of Murine Splenocytes

To investigate whether *Dioscorea* extracts modulate the immune system, the effects of DsCE-I, -II, and -III of *D. batatas* Decne on the proliferation of murine splenocytes were examined.

Female BALB/c mice, 8 to 12 weeks old, were purchased from the National Laboratory Animal Breeding and Research Center, Taipei, Taiwan, and maintained under standard pathogen-free conditions. Splenocytes were prepared from the mice according to the method described in Coligan et al. 1998, Current Protocols in Immunology. New York: John Wiley & Sons, Inc. with minor modifications. Briefly, the spleens of the mice were removed, minced at room temperature in an RPMI 1640 medium (Gibco BRL, Life Technologies, New York), and resuspended in the same medium. Tissue debris was removed by passing the cell suspension through a cotton column. Red blood cells were lyzed in an ACK buffer (150 mM $NH_4Cl$, 1.0 mM $KHCO_3$, 0.1 mM $Na_2EDTA$, pH 7.2). The splenocytes thus-obtained were grown in an RPMI 1640 medium supplemented with 10 mM HEPES (pH 7.0), non-essential amino acids (Gibco BRL, Life Technologies, New York), 50 µM β-mercaptoethanol, 0.03% L-glutamine, 50 µg/ml gentamycin (Gibco BRL, Life Technologies, New York), and 10% heat-inactivated (56° C., 30 min) fetal bovine serum (HyClone, Utah).

200 µl ($2 \times 10^5$) of splenocytes were seeded into individual wells of a 96-well plate and incubated with a medium containing 0, 100, 250, 500, or 1000 µg/ml of the extracts described above for 48 h. They were then labeled for 16 h with 1 µCi/well $^3$H-thymidine (specific activity 20 Ci/mmol, NET027X, NEN Life Science Products, Massachusetts). The labeled cells were harvested using a Cell Harvestor (Packard, Conn.) following the manufacturer's instructions. The radioactivity was determined using a TopCount•NXT™ system (Packard, Conn.). The $^3$H-thymidine incorporation was expressed as the radioactivity in cpm per well of the experimental group minus the cpm from the negative control (medium only) set.

In absence of pre-treatment with mitogens, such as phytohemagglutinin (PHA), concanavalin A (Con A), or cytokines, the DsCE-II fraction increased the proliferation of murine splenocytes in a linear, dose-dependent manner between 100 to 500 µg/ml. In contrast, DsCE-I failed to induce cell proliferation, and DsCE-III only slightly stimulated the proliferation.

The above-described DsCE-I, -II, and -III fractions were further examined for cytotoxicity on human skin fibroblast (CCD966SK), human hepatoma (Hep G2 and Huh 7), and human mammary carcinoma (MCF-7) cell lines using standard MTT assays (Vistica et al. (1991) Cancer Res. 51:2515-20). No cytotoxicity was found.

Synergy Between DsCE-II and IL-2

Murine splenocytes were prepared in the manner described above and incubated with media containing (1) an increasing amount of *D. batatas* Decne DsCE-II, (2) 2 ng/ml of recombinant mouse IL-2 (Biosource, Calif.), and (3) a combination of the extract and IL2, respectively. The proliferation of the splenocytes was examined in the same manner described above.

It was found that, at as low as 50 µg/ml, DsCE-II effectively stimulated the proliferation of the splenocytes induced by IL-2. The combined effect of IL-2 and DsCE-II on the proliferation of the splenocytes was always greater than the expected sum of the effects exerted by the two reagents individually. For example, the $^3$H-thymidine incorporation level of the splenocytes incubated with both 250 µg/ml DsCE-II and 2 ng/ml IL-2 was 4 times of the sum of the levels for splenocytes incubated with the same amounts of DsCE-II and IL-2, respectively.

In a reverse experimental design, a fixed concentration DsCE-II (250 µg/ml) was combined with varying doses of IL-2 (0-5 ng/ml). Similar synergistic effects on the proliferation of splenocytes were observed. In parallel experiments, extracts prepared from an Orchidaceae herb, *Anoectochilus formosanus*, were tested for their effects on splenocyte proliferation in the same manner. No synergy between them and IL-2 was detected. These results indicated that IL-2 and DsCE-II enhance the proliferation of splenocytes via a specific cellular mechanism(s), and that the enhancement is not due to general effects of a plant extract or a phytocompound fraction derived from it.

DsCE-II extracts prepared from the other three *Dioscorea* species or cultivars were also tested for their effects on splenocyte proliferation and their ability to enhance IL-2-mediated cell growth. Extracts from *D. alata* and *D. pseudojaponica* slightly stimulated splenocyte proliferation by themselves and showed no synergy with IL-2. In comparison, the extract from *D. alata* var. *purpurea* conferred a lower but significant effect. Among the DsCE-II extracts from the four species, *D. batatas* Decne DsCE-II exhibited the highest proliferation activity by itself and the highest synergy with IL-2.

*D. batatas* Decne DsCE-II Promoted Regeneration of Bone Marrow Cells and Splenocytes in 5-FU-treated Mice Female BALB/c mice were divided into several groups, 3 mice in each. At day 1, 5-fluorouracil (5-FU, F-6627, Sigma, Mo.) or water (as negative control) was injected intraperitoneally into the mice at a dose of 100 mg/kg body weight according to the method described in Wlodarski et al. 1998, Blood 91:2998-3006 and Cao et al. 1998 J. Interferon Cytokine Res. 18:227-233. 5-FU is a commonly used and potent chemotherapeutic drug for cancer patients.

As day 2, the mice were fed with *D. batatas* Decne DsCE-II at a daily does of 10 mg/kg body weight for five days. At day 7, the mice were sacrificed and bone marrow cells (BMCs) were isolated according to the protocols described in Randall and Weissman, 1997, Blood 89:3596-606 and Wlodarski et al. 1998, Blood 91:2998-3006. In brief, the femurs and tibias were dissected and the surrounding tissues removed. Both ends of each bone were cut and the marrow carefully flushed out with an RPMI medium using a syringe having a 25 G needle. Tissue debris and red blood cells were eliminated in the same manner described above. The number of BMC in each mouse was the then counted. The splenocytes from the mice were also isolated and counted. The results are summarized in Table 1 below:

TABLE 1

Effects of *D. batatas* Decne DsCE-II on murine bone marrow cells and splenocytes

| 5-FU Treatment | Extract | BMC ($\times 10^7$) | Splenocytes ($\times 10^7$) |
| --- | --- | --- | --- |
| No | None | 4.41 ± 0.42 | 7.54 ± 0.54 |
| Yes | None | 1.35 ± 0.26 | 2.98 ± 0.66 |
| Yes | DsCE-II | 2.94 ± 0.13 | 4.72 ± 0.39 |

As shown in Table 1, the average BMC and splenocyte counts in the mice treated with 5-FU and fed with DsCE-II were much higher than those in the mice treated with 5-FU but not fed with DsCE-II. The results indicate that *D. batatas* DsCE-II restores the BMC and splenocyte counts in 5-FU-treated mice.

Another experiment was conducted in the same manner described above, except that the 5-FU-treated mice were fed with *D. batatas* DsCE-I, *D. batatas* DsCE-II, and *D. alata* DsCE-II, respectively. The BMC and splenocyte counts in the mice were summarized in Table 2 below. The counts were presented as the percentages of those in the mice that were not treated 5-FU.

TABLE 2

Effects of *D. batatas* and *D. alata* extracts
on murine bone marrow cells and splenocytes

| 5-FU Treatment | Extract | BMC (%) | Splenocytes (%) |
|---|---|---|---|
| No | None | 100.0 | 100.0 |
| Yes | None | 24.6 | 47.1 |
| Yes | *D. batatas* DsCE-I | 24.8 | 50.6 |
| Yes | *D. batatas* DsCE-II | 49.1 | 75.2 |
| Yes | *D. alata* DsCE-II | 30.5 | 68.9 |

As shown in Table 2, *D. batatas* and *D. alata* DsCE-II extracts exhibited similar effects on splenocytes (75.2% and 68.9%). *D. batatas* DsCE-I had no or minimal effect on the count of BMCs or splenocytes. These results are analogous to that observed for the in vitro assay described above where DsCE-I exerted no effect on splenocyte proliferation. In contrast, the mice treated with 5-FU and fed with *D. batatas* DsCE-II had a significantly larger-BMC population than the mice treated with 5-FU but not fed with the extract (49.1 % vs. 24.6%). The mice treated with 5-FU and fed with *D. alata* DsCE-II also had a larger BMC population than those treated with 5-FU but not fed with any extract (30.5% vs. 24.6%). These results agree well with the above-described in vitro data showing that *D. batatas* DsCE-II has a higher activity than *D. alata* DsCE-II.

These results indicate that *D. batatas* and *D. alata* DsCE-IIs protect BMCs and splenocytes from 5-FU or promotes the regeneration of these cells after 5-FU treatment.

To further evaluate the effect of *D. batatas* DsCE-II on bone marrow cells, the response of the nucleated cells in bone marrow of the 5-FU-treated mice was examined according to the method described in Cao et al. 1998, J. Interferon Cytokine Res. 8:227-33. It was found that average count of the nucleated cells in the 5-FU-treated/DsCE-II fed mice was about 96% of that in the mice not treated with 5-FU. In comparison, the average nucleated bone marrow cell count in the mice treated with 5-FU and fed with a comparable dose of cucumber juice ("Veg") was much lower than that in the 5-FU-treated/DsCE-II fed mice.

DsCE-II Preferentially Stimulated Regeneration of Bone Marrow Progenitor Cells

The nucleated bone marrow cells described above were subsequently cultured in a M3434 medium and assayed for growth of colony forming unit (CFU) or progenitor cells, including CFU-GEMM, CFU-GM, and BFU-E following the manufacturer's instruction (StemCell; MethoCult™ GF M3434 media, Catalog #03434).

Briefly, nucleated bone marrow cells prepared from mouse femur and tibia were diluted in IMDM-2% FBS to a final density of $4 \times 10^5$ cells/ml. 0.3 ml of cell suspension was added to 3 ml of MethoCult™ GF M3434 media (StemCell, Catalog #03434). The mixtures were gently vortexed and allowed to stand for 5 to 10 minutes to dissipate air bubbles. Aliquots of 1.1 ml cell suspension were dispensed into 35 mm culture dishes (Nunclon™, Catalog #174926) using a syringe having an 18 G needle. The dishes were gently rotated to spread the cells onto the methylcellulose substratum evenly. Cell cultures were incubated in a humidified ($\geqq 95\%$)–5% $CO_2$ incubator at 37° C. for 12 days to generate cell colonies. Colony numbers and types were then determined using an inverted microscope (IX70, Olympus). The results from two independent experiments are summarized in Tables 3A and 3B below.

TABLE 3A

Effects of *D. batatas* extracts
on CFU-GM, BFU-E, and CFU-GEMM

| | | CFU number ($\times 10^{-2}$)/Hind limb | | |
|---|---|---|---|---|
| 5-FU Treatment | Fed with | GM | BFU-E | GEMM |
| No | $H_2O$ | 622.6 ± 83.6 | 17.8 ± 6.9 | 12.8 ± 5.5 |
| Yes | $H_2O$ | 336.2 ± 43.7 | 7.4 ± 0.6 | 6.7 ± 0.1 |
| Yes | Veg | 464.5 ± 45.2 | 11.2 ± 2.3 | 10.1 ± 1.5 |
| Yes | DsCEI | 491.9 ± 47.3 | 8.6 ± 3.0 | 11.2 ± 3.5 |
| Yes | DsCEII | 855.7 ± 132.1 | 12.9 ± 2.4 | 13.6 ± 2.2 |

TABLE 3B

Effects of *D. batatas* extracts DsCE-II
on CFU-GM, BFU-E, and CFU-GEMM

| | | CFU number ($\times 10^{-2}$)/Hind limb | | |
|---|---|---|---|---|
| 5-FU Treatment | Fed with | GM | BFU-E | GEMM |
| No | $H_2O$ | 337.7 ± 5 | 26.7 ± 0.5 | 15.4 ± 3.7 |
| Yes | $H_2O$ | 169.2 ± 47.3 | 6.9 ± 0.8 | 4.3 ± 1.3 |
| Yes | DsCE-II | 366.5 ± 174.6 | 15 ± 5.2 | 7.5 ± 0.5 |

As shown in Tables 3A and B, the colony numbers of CFU-GM, BFU-E, and CFU-GEMM for the 5-FU treated mice were substantially smaller (by about 50%) than those for the mice not treated with 5-FU. For the 5-FU-treated/DsCE-II fed mice, the CFU-GM, BFU-E, and CFU-GEMM colony numbers were higher than those for the mice not fed with the extract. In particular, the CFU-GM and CFU-GEMM colony numbers were even higher than those for the mice not treated with 5-FU. These results indicate that *D. batatas* DsCE-II specifically stimulates the regeneration of CFU-GM and CFU-GEMM cell lineages, and, to a lesser degree, that of BFU-E lineage.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of enhancing proliferation of bone marrow cells or spleen cells, the method comprising identifying a subject in need of enhancing proliferation of bone marrow or spleen cells and administering to the subject an effective amount of a DsCEII extract from a tuber of a *Dioscorea* plant, wherein the DsCEII extract is prepared by a process including:
   a) obtaining an aqueous extract of a tuber of a *Dioscorea* plant,
   b) extracting the extract of part (a) with an aqueous solution containing 50% ethanol to form a first supernatant and first ethanol-insoluble fraction, c) extracting said first supernatant of part (b) with an aqueous solution containing 75% ethanol to form a second supernatant and a second ethanol-insoluble fraction and d) collecting said second ethanol-insoluble fraction, wherein the second ethanol-insoluble fraction is DsCEII, and wherein the *Dioscorea* plant is selected from the group consisting of *Dioscorea batatas* Decne, *Dioscorea alata* L., *Dioscorea pseudojaponica*, and *Dioscorea alata* L. var. *purpurea* (Roxb.) M. Pouch.

2. The method of claim 1, wherein the bone marrow cells are CFU-GM, CFU-GEMM, or CFU-BFU-E cells.

3. A method of enhancing proliferation of bone marrow cells or spleen cells, the method comprising administering to a subject in need thereof an effective amount of a DsCEII extract from a tuber of a *Dioscorea* plant and an effective amount of a cytokine, wherein the DsCEII extract is prepared by a process including:

a) obtaining an aqueous extract of a tuber of a *Dioscorea* plant, b) extracting the extract of part (a) with an aqueous solution containing 50% ethanol to form a first supernatant and first ethanol-insoluble fraction, c) extracting said first supernatant of part (b) with an aqueous solution containing 75% ethanol to form a second supernatant and a second ethanol-insoluble fraction and d) collecting said second ethanol-insoluble fraction, wherein the second ethanol-insoluble fraction is DsCEII, and wherein the *Dioscorea* plant is selected from the group consisting of *Dioscorea batatas* Decne, *Dioscorea alata* L., *Dioscorea pseudojaponica*, and *Dioscorea alata* L. var. *purpurea* (Roxb.) M. Pouch.

4. The method of claim 3, wherein the cytokine is interleukin-2.

5. The method of claim 4, wherein the *Dioscorea* plant is *Duiscirea batatas*.

6. The method of claim 3, wherein the bone marrow cells are CFU-GM, CFU-GEMM, or CFU-BFU-E cells.

7. The method of claim 6, wherein the cytokine is interleukin-2.

8. The method of claim 7, wherein the *Dioscorea* plant is *Dioscorea batatas*.

* * * * *